(12) United States Patent
Hassan et al.

(10) Patent No.: US 8,153,077 B2
(45) Date of Patent: Apr. 10, 2012

(54) SYSTEM AND PROCESS FOR PRODUCTION OF NITROBENZENE

(75) Inventors: Abbas Hassan, Sugar Land, TX (US);
Ebrahim Bagherzadeh, Sugar Land, TX (US); Rayford G. Anthony, College Station, TX (US); Gregory G. Borsinger, Chatham, NJ (US); Aziz Hassan, Sugar Land, TX (US)

(73) Assignee: H R D Corporation, Houston, TX (US)

( * ) Notice: Subject to any disclaimer, the term of this patent is extended or adjusted under 35 U.S.C. 154(b) by 0 days.

(21) Appl. No.: 12/568,280

(22) Filed: Sep. 28, 2009

(65) Prior Publication Data
US 2010/0015015 A1 Jan. 21, 2010

Related U.S. Application Data

(62) Division of application No. 12/138,941, filed on Jun. 13, 2008, now Pat. No. 7,696,391.

(60) Provisional application No. 60/946,446, filed on Jun. 27, 2007.

(51) Int. Cl.
*B01J 19/18* (2006.01)

(52) U.S. Cl. .......... 422/225; 422/135; 366/342; 44/301; 44/302; 516/197

(58) Field of Classification Search .................. 422/225, 422/135; 366/364, 342, 302; 44/301, 302; 516/197
See application file for complete search history.

(56) References Cited

U.S. PATENT DOCUMENTS

| 2,256,999 | A | * | 9/1941 | Castner | 568/937 |
|---|---|---|---|---|---|
| 3,296,168 | A | * | 1/1967 | Jirik et al. | 524/561 |
| 3,781,320 | A | | 12/1973 | Irwin | |
| 3,892,798 | A | * | 7/1975 | Heeg et al. | 560/94 |
| 3,928,475 | A | * | 12/1975 | Dassel | 568/939 |
| 3,963,640 | A | * | 6/1976 | Smith | 516/79 |
| 4,021,498 | A | * | 5/1977 | Alexanderson et al. | 568/939 |
| 4,571,437 | A | * | 2/1986 | Caskey et al. | 564/418 |
| 4,724,269 | A | | 2/1988 | Suzki et al. | |
| 4,740,621 | A | * | 4/1988 | Adams et al. | 564/419 |

(Continued)

FOREIGN PATENT DOCUMENTS
EP 1604969 A 12/2005
(Continued)

OTHER PUBLICATIONS

IKA—Rotor?Stator Generators—2003 Process Catalog.*

(Continued)

*Primary Examiner* — Walter D Griffin
*Assistant Examiner* — Huy-Tram Nguyen
(74) *Attorney, Agent, or Firm* — Timothy S. Westby; Porter Hedges LLP

(57) ABSTRACT

A method for producing nitrobenzene is disclosed which comprises forming a dispersion comprising benzene-containing droplets or particles dispersed in a mixture of concentrated nitric acid and concentrated sulfuric acid, wherein said particles have a mean diameter less than one micron, and subjecting the dispersion to reaction conditions comprising a pressure in the range of about 203 kPa (2 atm) to about 6080 kPa (60 atm) and a temperature in the range of about 20° C. to about 230° C., whereby at least a portion of said benzene is nitrated to form nitrobenzene. A system for carrying out the method is also disclosed.

20 Claims, 2 Drawing Sheets

U.S. PATENT DOCUMENTS

| | | | | |
|---|---|---|---|---|
| 4,772,757 A * | 9/1988 | Lailach et al. | | 568/939 |
| 4,886,905 A | 12/1989 | Larkins, Jr. | | |
| 4,914,029 A | 4/1990 | Caransa et al. | | |
| 4,950,831 A | 8/1990 | Staton et al. | | |
| 4,973,770 A * | 11/1990 | Evans | | 568/929 |
| 5,004,846 A | 4/1991 | Sato et al. | | |
| 5,009,816 A | 4/1991 | Weise et al. | | |
| 5,030,776 A | 7/1991 | Sato et al. | | |
| 5,081,303 A * | 1/1992 | Greenfield et al. | | 564/419 |
| 5,140,674 A * | 8/1992 | Anderson et al. | | 358/1.12 |
| 5,264,087 A | 11/1993 | Lowery et al. | | |
| 5,313,009 A * | 5/1994 | Guenkel et al. | | 568/927 |
| 5,382,358 A | 1/1995 | Yeh | | |
| 5,451,348 A | 9/1995 | Kingsley | | |
| 5,498,766 A * | 3/1996 | Stuart et al. | | 435/99 |
| 5,531,425 A * | 7/1996 | Skibo et al. | | 266/208 |
| 5,616,807 A * | 4/1997 | Foster et al. | | 564/423 |
| 5,696,305 A * | 12/1997 | Klingler et al. | | 568/934 |
| 5,710,355 A | 1/1998 | Krishnamurti | | |
| 5,756,714 A | 5/1998 | Antrim et al. | | |
| 5,763,697 A * | 6/1998 | Hermann et al. | | 568/939 |
| 5,877,350 A * | 3/1999 | Langer et al. | | 564/423 |
| 6,187,825 B1 * | 2/2001 | Guntherberg et al. | | 516/197 |
| 6,194,625 B1 | 2/2001 | Graves et al. | | |
| 6,251,289 B1 | 6/2001 | Sherman | | |
| 6,368,366 B1 * | 4/2002 | Langer et al. | | 44/301 |
| 6,368,367 B1 * | 4/2002 | Langer et al. | | 44/301 |
| 6,383,237 B1 * | 5/2002 | Langer et al. | | 44/301 |
| 6,530,964 B2 | 3/2003 | Langer et al. | | |
| 6,693,213 B1 | 2/2004 | Kolena et al. | | |
| 6,742,774 B2 | 6/2004 | Holl | | |
| 6,768,021 B2 | 7/2004 | Horan et al. | | |
| 6,787,036 B2 | 9/2004 | Long | | |
| 6,809,217 B1 | 10/2004 | Colley et al. | | |
| 7,473,348 B2 * | 1/2009 | Koch | | 208/113 |
| 2001/0020344 A1 * | 9/2001 | Thompson et al. | | 44/301 |
| 2003/0043690 A1 | 3/2003 | Holl | | |
| 2004/0052158 A1 | 3/2004 | Holl | | |
| 2005/0033069 A1 | 2/2005 | Holl et al. | | |
| 2005/0150155 A1 * | 7/2005 | Waldron et al. | | 44/301 |
| 2006/0041166 A1 * | 2/2006 | Stuart | | 560/348 |
| 2006/0245991 A1 * | 11/2006 | Holl et al. | | 422/225 |
| 2006/0272634 A1 | 12/2006 | Nehmer et al. | | |
| 2007/0030322 A1 * | 2/2007 | Lee et al. | | 347/88 |
| 2007/0294935 A1 * | 12/2007 | Waldron et al. | | 44/301 |
| 2008/0116116 A1 * | 5/2008 | Koch | | 208/351 |

FOREIGN PATENT DOCUMENTS

| | | | |
|---|---|---|---|
| JP | 61183235 A | 8/1986 |
| JP | 2300149 A | 12/1990 |
| JP | 2000143706 A | 5/2000 |
| JP | 2002003505 A | 1/2002 |
| JP | 2002121353 A | 4/2002 |
| JP | 2007505201 A | 3/2007 |
| WO | 98043725 A | 10/1998 |
| WO | 2005108533 A2 | 11/2005 |
| WO | 2007023864 Y | 3/2007 |

OTHER PUBLICATIONS

Rotor-Stator Generators for Batch, In-Line Mixing by IKA—Apr. 14, 2010.*
Office Action Dated Apr. 20, 2010 for U.S. Appl. No. 12/411,660.
Office Action Dated Apr. 20, 2010 for U.S. Appl. No. 12/427,286.
Office Action Dated Apr. 23, 2010 for U.S. Appl. No. 12/568,155.
Office Action Dated Apr. 27, 2010 for U.S. Appl. No. 12/568,280.
Office Action Dated May 5, 2010 for U.S. Appl. No. 12/142,120.
Office Action Dated Jun. 25, 2009 for U.S. Appl. No. 12/142,447.
Office Action Dated Jan. 7, 2010 for U.S. Appl. No. 12/142,447.
Office Action Dated May 13, 2010 for U.S. Appl. No. 12/142,447.
Office Action Dated Feb. 4, 2010 for U.S. Appl. No. 12/492,721.
Office Action Dated Feb. 18, 2010 for U.S. Appl. No. 12/635,433.
Office Action Dated Feb. 18, 2010 for U.S. Appl. No. 12/635,454.
Office Action Dated May 14, 2010 for U.S. Appl. No. 12/137,441.
Office Action Dated Feb. 19, 2010 for U.S. Appl. No. 12/144,459.
Office Action Dated Sep. 2, 2009 for U.S. Appl. No. 12/142,433.
Office Action Dated Jan. 29, 2010 for U.S. Appl. No. 12/142,433.
Office Action Dated May 24, 2010 for U.S. Appl. No. 12/142,433.
Office Action Dated Apr. 30, 2010 for U.S. Appl. No. 12/141,191.
Office Action Dated Oct. 27, 2009 for U.S. Appl. No. 12/142,120.
Office Action Dated May 5, 2010 for U.S. Appl. No. 12/571,537.
Gogate et al., "Cavitation: A technology on the horizon," Current Science 91 (No. 1); 35-46 (2006.
PCT Search Report and Written Opinion dated Aug. 29, 2008 for corresponding PCT Application No. PCT/US2008/066909 (6 pgs.).
Canadian Office Action dated Jul. 11, 2011 for corresponding Canadian Application No. 2,692,280 (2 pgs.).

* cited by examiner

SYSTEM AND PROCESS FOR PRODUCTION OF NITROBENZENE

CROSS-REFERENCE TO RELATED APPLICATIONS

This application is a divisional application which claims the benefit under 35 U.S.C. §121 of U.S. patent application Ser. No. 12/138,941, filed Jun. 13, 2008, which claims the benefit under 35 U.S.C. §119(e) of U.S. Provisional Patent Application No. 60/946,446 filed Jun. 27, 2007, the disclosures of each of which are hereby incorporated herein by reference.

STATEMENT REGARDING FEDERALLY SPONSORED RESEARCH OR DEVELOPMENT

Not Applicable.

TECHNICAL FIELD

The present invention generally relates to apparatus and methods for producing nitrobenzene by liquid phase reaction of benzene with nitric acid and sulfuric acid, and more particularly to the acceleration of such reaction by utilization of high shear mixing.

BACKGROUND OF THE INVENTION

Nitrobenzene ($C_6H_5NO_2$) is an aromatic compound that is widely used as a solvent and as a mild oxidizing agent. In the chemical industry it is primarily used in the production of aniline and aniline derivatives, such as methylene diphenyl diisocyanate (MDI); however, it also finds use in the manufacture of other chemicals, rubber, pesticides, dyes and pharmaceuticals. In the pharmaceutical industry nitrobenzene is used, for instance, in the production of the analgesic paracetamol (acetaminophen).

The most common reagent used in conventional methods for preparing nitrobenzene is nitric acid or a mixed acid, typically, a mixed solution of concentrated nitric acid and concentrated sulfuric acid, oleum or fuming sulfuric acid. The process generally includes initially forming a nitronium ion, $NO_2^+$ by the reaction of nitric acid with concentrated sulfuric acid, as follows:

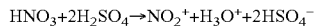

The nitronium ion then reacts with benzene to form nitrobenzene, according to the following reaction:

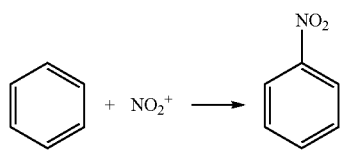

This mixture of acids forms an electrophile which reacts with the benzene in an aromatic electrophilic substitution reaction known as a nitration reaction. The nitric acid is protonated by the sulfuric acid to form $H_2NO_3^+$, which then loses water to form $NO_2^+$. The concentrated sulfuric acid has a high affinity for the water, which facilitates the reaction. Following formation of nitrobenzene, it may be separated from spent and unspent acids by drawing off the sulfuric acid, and returning it to the benzene nitration process as concentrated sulfuric acid.

Such processes are strongly influenced by a number of factors, such as temperatures, and pressures. Appropriate selection of these factors is important, as selection influences the reaction trend, the reaction velocity, and the overall technical and economic balance of the production, in terms of yield, and catalyst consumption, if applicable, and also from the point of view of the intricacy and costs of installation and upkeep. These costs are influenced, for example, by the pressures attained, the consumption of thermal energy for reaching desired temperatures, and the intricacy and the number of component parts of the installation. For instance, in many applications it is desirable to enhance the degree of conversion of benzene. While increasing the reaction pressure may increase reaction rate, it also increases wear of the materials constituting the reactors, the pipings, and the mechanical parts of the plant, as well as any ancillary devices. Most existing processes and production facilities for making nitrobenzene are subject to a variety of constraints such as product yield, plant size, energy consumption and mass flow limitations. Accordingly, there is continuing interest in improving the ways that nitrobenzene is produced.

SUMMARY

Systems and methods for accelerating production of nitrobenzene are disclosed. In accordance with certain embodiments of the invention, a method of producing nitrobenzene comprises forming a nanoemulsion comprising benzene-containing particles dispersed in a mixture of concentrated nitric acid and concentrated sulfuric acid, wherein said particles have a mean diameter less than 1 micron; and subjecting said nanoemulsion to reaction conditions comprising a pressure in the range of about 203 kPa (2 atm) to about 6080 kPa (60 atm) and a temperature in the range of about 20° C. to about 230° C., whereby at least a portion of said benzene is nitrated to form nitrobenzene.

In accordance with certain embodiments of the invention, a system for production of nitrobenzene is provided which comprises at least one high shear mixing device configured for producing a nanoemulsion comprising benzene-containing particles dispersed in a mixture of concentrated nitric acid and concentrated sulfuric acid, wherein said particles have a mean diameter less than 1 micron; and a reaction vessel. Embodiments of the methods and apparatus potentially provide overall cost reduction by operating at lower temperature and/or pressure, providing increased product per unit of reactants consumed, decreased reaction time, and/or reduced capital and/or operating costs. These and other embodiments and potential advantages will be apparent in the following detailed description and drawings.

DETAILED DESCRIPTION

The present processes and systems for the production of nitrobenzene via liquid phase reaction of benzene with a mixture of nitric and sulfuric acids via an external high shear mechanical device to provide rapid contact and mixing of the chemical ingredients in a controlled environment in a high shear mixing device, which may also serve as a reactor. The high shear device reduces the mass transfer limitations on the reaction and thus increases the overall reaction rate.

Chemical reactions involving liquids, gases and solids rely on the laws of kinetics that involve time, temperature, and pressure to define the rate of reactions. In applications where it is desirable to react two or more raw materials of different phases (e.g. solid and liquid; liquid and gas; solid, liquid and gas), one of the limiting factors in controlling the rate of reaction involves the contact time of the reactants. In the case of heterogeneously catalyzed reactions there is the additional rate limiting factor of having the reacted products removed from the surface of the catalyst to enable it to catalyze further reactants. Contact time for the reactants and/or catalyst is often controlled by mixing which provides contact with two or more reactants involved in a chemical reaction. Homogeneous reactions (e.g., liquid-liquid phase) may also benefit from high shear mixing, as disclosed herein, by at least providing uniform temperature distribution within the reactor and minimizing potential side reactions. Accordingly, in some embodiments, a high shear process as described herein promotes homogeneous reaction(s).

A reactor assembly that comprises an external high shear mixing device or mixer as described herein makes possible decreased mass transfer limitations and thereby allows the reaction to more closely approach kinetic limitations. When reaction rates are accelerated, residence times may be decreased, thereby increasing obtainable throughput of the process. Product yield may be increased as a result of the high shear system and process. Alternatively, if the product yield of an existing process is acceptable, decreasing the required residence time by incorporation of suitable/high shear mixing may allow for the use of lower temperatures and/or pressures than conventional processes.

System for Production of Nitrobenzene

Figure 1:
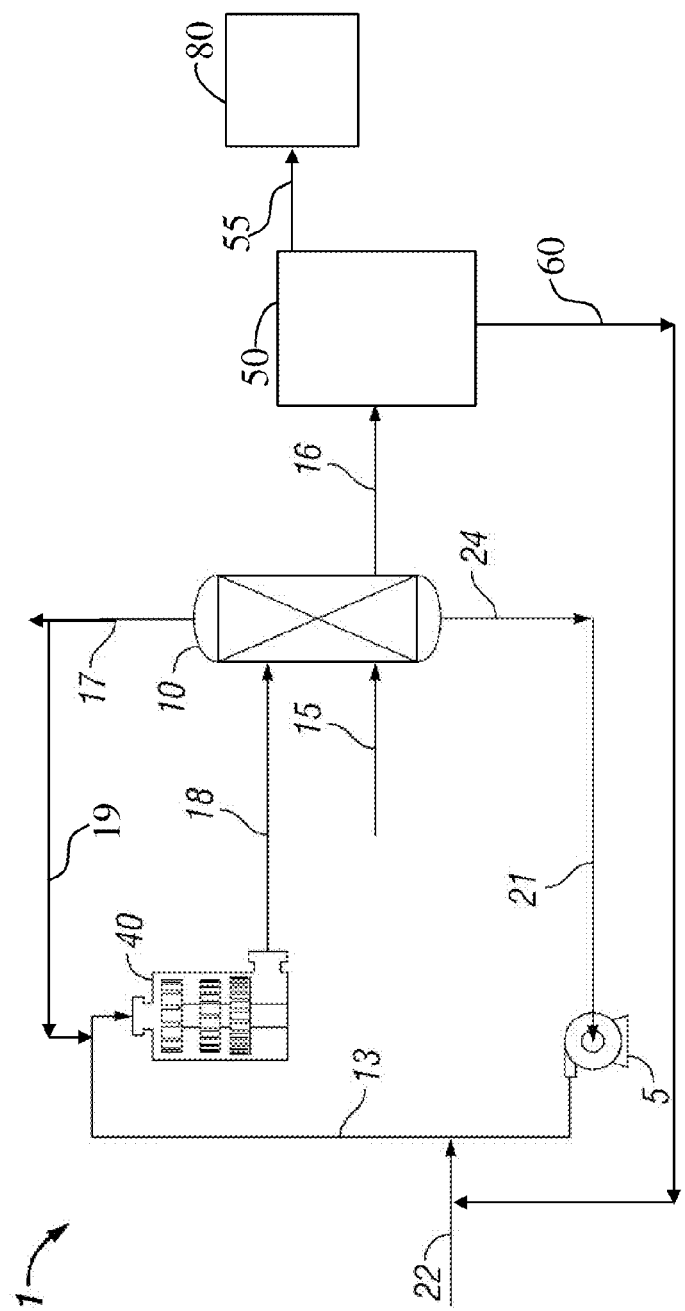
FIG. 1 is a process flow diagram of a process for production of nitrobenzene, according to certain embodiments of the invention.

A high shear nitrobenzene production system will now be described in relation to FIG. 1, which is a process flow diagram of an embodiment of a high shear system 1 for the production of nitrobenzene by liquid phase reaction of benzene with concentrated nitric and sulfuric acids. The basic components of a representative system include external high shear mixing device (HSD) 40, vessel 10, and pump 5. As shown in FIG. 1, the high shear device is located external to vessel/reactor 10. Each of these components is further described in more detail below. Line 21 is connected to pump 5 for introducing a liquid stream comprising a mixture of concentrated nitric acid and concentrated sulfuric acid. Line 13 connects pump 5 to HSD 40, and line 18 connects HSD 40 to vessel 10. Line 22 is connected to line 13 for introducing benzene liquid. Line 17 is connected to vessel 10 for removal of vent gas containing unreacted benzene vapor and any other reaction gases. Additional components or process steps may be incorporated between vessel 10 and HSD 40, or ahead of pump 5 or HSD 40, if desired.

High Shear Mixing Device. External high shear mixing device (HSD) 40, also sometimes referred to as a high shear mixer, is configured for receiving an inlet stream via line 13, comprising benzene and concentrated nitric and sulfuric acids. Alternatively, HSD 40 may be configured for receiving the liquid reactant streams via separate inlet lines (not shown). Although only one high shear device is shown in FIG. 1, it should be understood that some embodiments of the system may have two or more high shear mixing devices arranged either in series or parallel flow. HSD 40 is a mechanical device that utilizes one or more generators comprising a rotor/stator combination, each of which having a fixed gap between the stator and rotor. HSD 40 is configured in such a way that it is capable of producing an emulsion containing submicron (i.e., less than one micron in diameter) and micron-sized particles containing benzene dispersed in a reactant mixture flowing through the mixer. The high shear mixer comprises an enclosure or housing so that the pressure and temperature of the reaction mixture may be controlled.

High shear mixing devices are generally divided into three general classes, based upon their ability to mix fluids. Mixing is the process of reducing the size of particles or inhomogeneous species within the fluid. One metric for the degree or thoroughness of mixing is the energy density per unit volume that the mixing device generates to disrupt the fluid particles. The classes are distinguished based on delivered energy densities. Three classes of industrial mixers having sufficient energy density to consistently produce mixtures or emulsions with particle sizes in the range of submicron to 50 microns include homogenization valve systems, colloid mills and high speed mixers. In the first class of high energy devices, referred to as homogenization valve systems, fluid to be processed is pumped under very high pressure through a narrow-gap valve into a lower pressure environment. The pressure gradients across the valve and the resulting turbulence and cavitation act to break-up any particles in the fluid. These valve systems are most commonly used in milk homogenization and can yield average particle sizes in the 0-1 micron range.

At the opposite end of the energy density spectrum is the third class of devices referred to as low energy devices. These systems usually have paddles or fluid rotors that turn at high speed in a reservoir of fluid to be processed, which in many of the more common applications is a food product. These low energy systems are customarily used when average particle sizes of greater than 20 microns are acceptable in the processed fluid.

Between the low energy devices and homogenization valve systems, in terms of the mixing energy density delivered to the fluid, are colloid mills, which are classified as intermediate energy devices. A typical colloid mill configuration includes a conical or disk rotor that is separated from a complementary, liquid-cooled stator by a closely-controlled rotor-stator gap, which is commonly between 0.0254 mm-10.16 mm (0.001-0.40 inch). Rotors are usually driven by an electric motor through a direct drive or belt mechanism. As the rotor rotates at high rates, it pumps fluid between the outer surface of the rotor and the inner surface of the stator, and shear forces generated in the gap process the fluid. Many colloid mills with proper adjustment achieve average particle sizes of 0.1-25 microns in the processed fluid. These capabilities render colloid mills appropriate for a variety of applications including colloid and oil/water-based emulsion processing such as that required for cosmetics, mayonnaise, or silicone/silver amalgam formation, to roofing-tar mixing.

An approximation of energy input into the fluid (kW/L/min) can be estimated by measuring the motor energy (kW) and fluid output (L/min). Tip speed is the circumferential distance traveled by the tip of the rotor per unit of time. Tip speed is thus a function of the rotor diameter and the rotational frequency. Tip speed (in meters per minute, for example) may be calculated by multiplying the circumferential distance transcribed by the rotor tip, $2\pi R$, where R is the radius of the rotor (in meters, for example) times the frequency of revolution (in revolutions per minute). A colloid mill, for example, may have a tip speed in excess of 22.9 m/sec (4500 ft/min) and may exceed 40 m/sec (7900 ft/min). For the purposes of this disclosure, the term "high shear"

refers to mechanical rotor stator devices (e.g., colloid mills or rotor/stator mixers) that are capable of tip speeds in excess of 5.1 m/sec. (1000 ft/min) and require an external mechanically driven power device to drive energy into the stream of materials to be reacted. For example, in HSD 40, a tip speed in excess of 22.9 m/sec (4500 ft/min) is achievable, and may exceed 40 m/sec (7900 ft/min). In some embodiments, HSD 40 is capable of delivering at least 300 L/h with a power consumption of about 1.5 kW at a nominal tip speed of at least 22.9 m/sec (4500 ft/min).

HSD 40 combines high tip speeds with a very small shear gap to produce significant shear on the material being processed. The amount of shear will be dependant on the viscosity of the fluid. Accordingly, a local region of elevated pressure and temperature is created at the tip of the rotor during operation of the high shear device. In some cases the locally elevated pressure is about 1034.2 MPa (150,000 psi). In some cases the locally elevated temperature is about 500° C. In some cases these local pressure and temperature elevations may persist for nano or pico seconds. In some embodiments, the energy expenditure of the high shear mixer is greater than 1000 W/m$^3$. In embodiments, the energy expenditure of HSD 40 is in the range of from about 3000 W/m$^3$ to about 7500 W/m$^3$. The shear rate is the tip speed divided by the shear gap width (minimal clearance between the rotor and stator). The tip shear rate generated in HSD 40 may be greater than 20,000 s$^{-1}$. In some embodiments the shear rate is at least 1,600,000 s$^{-1}$. In embodiments, the shear rate generated by HSD 40 is in the range of from 20,000 s$^{-1}$ to 100,000 s$^{-1}$. For example, in one application the rotor tip speed is about 40 m/sec (7900 ft/min) and the shear gap width is 0.0254 mm (0.001 inch), producing a shear rate of 1,600,000 s$^{-1}$. In another application the rotor tip speed is about 22.9 m/sec (4500 ft/min) and the shear gap width is 0.0254 mm (0.001 inch), producing a shear rate of about 901,600 s$^{-1}$.

HSD 40 is capable of highly emulsifying benzene into a main liquid phase comprising concentrated nitric acid and concentrated sulfuric acid, in some cases together with a soluble catalyst or catalyst slurry, with which the benzene would normally be immiscible, at conditions such that at least a portion of the benzene reacts with the nitronium ions produced by the concentrated acids, to produce a product stream comprising nitrobenzene. In some embodiments, HSD 40 comprises a colloid mill. Suitable colloidal mills are manufactured by IKA® Works, Inc. Wilmington, N.C. and APV North America, Inc. Wilmington, Mass., for example. In some instances, HSD 40 comprises the DISPAX REACTOR® of IKA® Works, Inc. Several models are available having various inlet/outlet connections, horsepower, nominal tip speeds, output rpm, and nominal flow rate. Selection of a particular device will depend on specific throughput requirements for the intended application, and on the desired droplet size in the outlet dispersion from the high shear mixer. In some embodiments, selection of the appropriate mixing tools (generators) within HSD 40 may allow for catalyst size reduction/increase in catalyst surface area.

The high shear device comprises at least one revolving element that creates the mechanical force applied to the reactants. The high shear device comprises at least one stator and at least one rotor separated by a clearance. For example, the rotors may be conical or disk shaped and may be separated from a complementary-shaped stator. Both the rotor and stator may comprise a plurality of circumferentially-spaced teeth. In some embodiments, the stator(s) are adjustable to obtain the desired gap between the rotor and the stator of each generator (rotor/stator set). Grooves in the rotor and/or stator may change directions in alternate stages for increased turbulence. Each generator may be driven by any suitable drive system configured for providing the necessary rotation.

In some embodiments, the minimum clearance between the stator and the rotor is in the range of from about 0.0254 mm to about 3.175 mm (about 0.001 inch to about 0.125 inch). In certain embodiments, the minimum clearance between the stator and rotor is about 1.524 mm (0.060 inch). In certain configurations, the minimum clearance between the rotor and stator is at least 1.778 mm (0.07 inch). The shear rate produced by the high shear mixer may vary with longitudinal position along the flow pathway. In some embodiments, the rotor is set to rotate at a speed commensurate with the diameter of the rotor and the desired tip speed. In some embodiments, the colloidal mill has a fixed clearance between the stator and rotor. Alternatively, the colloid mill has adjustable clearance.

In some embodiments, HSD 40 comprises a single stage dispersing chamber (i.e., a single rotor/stator combination, a single generator). In some embodiments, high shear device 40 is a multiple stage inline colloid mill and comprises a plurality of generators. In certain embodiments, HSD 40 comprises at least two generators. In other embodiments, high shear device 40 comprises at least 3 high shear generators. In some embodiments, high shear device 40 is a multistage mixer whereby the shear rate (which varies proportionately with tip speed and inversely with rotor/stator gap) varies with longitudinal position along the flow pathway, as further described herein below.

In some embodiments, each stage of the external high shear device has interchangeable mixing tools, offering flexibility. For example, the DR 2000/4 DISPAX REACTOR® of IKA® Works, Inc. Wilmington, N.C. and APV North America, Inc. Wilmington, Mass., comprises a three stage dispersing module. This module may comprise up to three rotor/stator combinations (generators), with choice of fine, medium, coarse, and super-fine for each stage. This allows for creation of dispersions having a narrow distribution of the desired bubble size, or liquid-liquid phase emulsions containing particles of the desired size. In some embodiments, each of the stages is operated with super-fine generator. In some embodiments, at least one of the generator sets has a rotor/stator minimum clearance of greater than about 5.08 mm (0.20 inch). In some embodiments, at least one of the generator sets has a minimum rotor/stator clearance of greater than about 1.778 mm (0.07 inch). In some embodiments the rotors are 60 mm and the are stators 64 mm in diameter, providing a clearance of about 4 mm.

Figure 2:
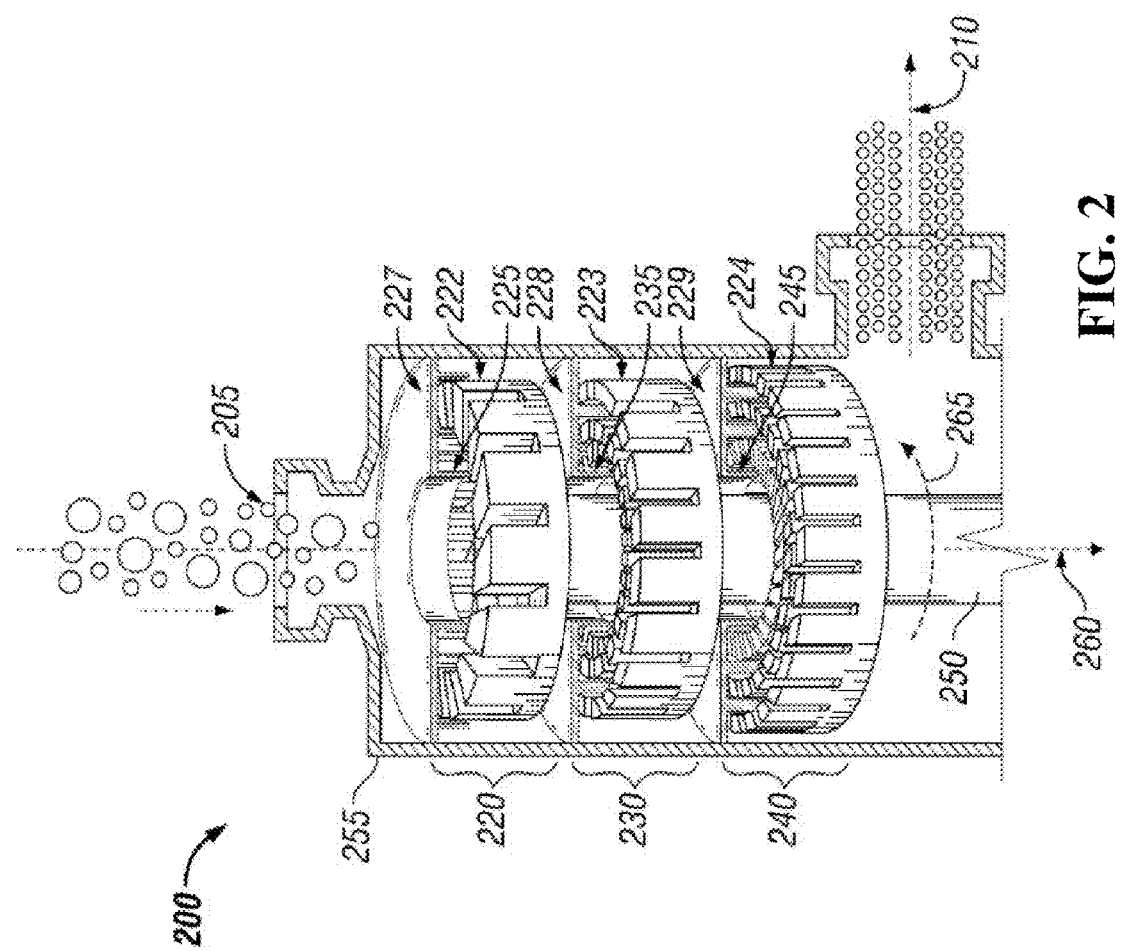
FIG. 2 is a longitudinal cross-section view of a multi-stage high shear device, as employed in an embodiment of the system of FIG. 1.

Referring now to FIG. 2, there is presented a longitudinal cross-section of a suitable high shear device 200. High shear device 200 is a dispersing device comprising three stages or rotor-stator combinations, 220, 230, and 240. Three rotor/stator sets or generators 220, 230, and 240 are aligned in series along drive input 250. The first generator 220 comprises rotor 222 and stator 227. The second generator 230 comprises rotor 223, and stator 228; the third generator 240 comprises rotor 224 and stator 229. For each generator the rotor is rotatably driven by input 250 and rotates, as indicated by arrow 265, about axis 260. Stator 227 is fixedly coupled to high shear device wall 255. Each generator has a shear gap which is the distance between the rotor and the stator. First generator 220, comprises a first shear gap 225; second generator 230 comprises a second shear gap 235; and third generator 240 comprises a third shear gap 245. In some embodiments, shear gaps 225, 235, 245 are between about 0.025 mm and 10.0 mm wide. In some embodiments, the process comprises utilization of a high shear device 200 wherein the gaps 225, 235, 245 are between about 0.5 mm and about 2.5 mm.

In certain instances the gap is maintained at about 1.5 mm. Alternatively, the gaps 225, 235, 245 are different for generators 220, 230, 240. In certain instances, the gap 225 for the first generator 220 is greater than about the gap 235 for the second generator 230, which is in turn greater than about the gap 245 for the third generator. As mentioned above, the generators of each stage may be interchangeable, offering flexibility.

Generators 220, 230, and 240 may comprise a coarse, medium, fine, and super-fine characterization. Rotors 222, 223, and 224 and stators 227, 228, and 229 may be toothed designs. Each generator may comprise two or more sets of rotor-stator teeth. Rotors 222, 223, and 224 may comprise a number of rotor teeth circumferentially spaced about the circumference of each rotor. Stators 227, 228, and 229 may comprise a complementary number of stator teeth circumferentially spaced about the circumference of each stator. In embodiments, the inner diameter of the rotor is about 11.8 cm. In embodiments, the outer diameter of the stator is about 15.4 cm. In certain embodiments, each of three stages is operated with a super-fine generator, comprising a shear gap of between about 0.025 mm and about 3 mm. For applications in which solid particles are to be sent through high shear device 200, shear gap width may be selected for reduction in particle size and increase in particle surface area. In some embodiments, the disperser is configured so that the shear rate will increase stepwise longitudinally along the direction of the flow. The IKA® model DR 2000/4, for example, comprises a belt drive, 4M generator, PTFE sealing ring, inlet flange 25.4 mm (1 inch) sanitary clamp, outlet flange 19 mm (¾ inch) sanitary clamp, 2HP power, output speed of 7900 rpm, flow capacity (water) approximately 300-700 L/h (depending on generator), a tip speed of from 9.4-41 m/sec (1850 ft/min to 8070 ft/min).

Vessel. Vessel or reactor 10 is any type of vessel in which a multiphase reaction can be propagated to carry out the above-described conversion reaction(s). For instance, a continuous or semi-continuous stirred tank reactor, or one or more batch reactors may be employed in series or in parallel. In some applications vessel 10 may be a tower reactor, and in others a tubular reactor or multi-tubular reactor. One or more line 15 may be connected to vessel 10 for introducing the concentrated sulfuric acid and the concentrated nitric acid, or for injecting water, or other material (e.g., a catalyst).

Vessel 10 may include one or more of the following items: stirring system, heating and/or cooling capabilities, pressure measurement instrumentation, temperature measurement instrumentation, one or more injection points, and level regulator (not shown), as are known in the art of reaction vessel design. For example, a stirring system may include a motor driven mixer. A heating and/or cooling apparatus may comprise, for example, a heat exchanger. Alternatively, as much of the conversion reaction may occur within HSD 40 in some embodiments, vessel 10 may serve primarily as a storage vessel in some cases. Although generally less desired, in some applications vessel 10 may be omitted, particularly if multiple high shear mixers/reactors are employed in series, as further described below. Line 16 is connected to vessel 10 for withdrawal or removal of reaction product containing nitrobenzene. In some embodiments, a separating tank 50 may be connected to vessel 10 by line 16, for separation and removal of unreacted benzene 60, which may be recycled to HSD 40, if desired.

Heat Transfer Devices. In addition to the above-mentioned heating/cooling capabilities of vessel 10, other external or internal heat transfer devices for heating or cooling a process stream are also contemplated in variations of the embodiments illustrated in FIG. 1. Some suitable locations for one or more such heat transfer devices are between pump 5 and HSD 40, between HSD 40 and vessel 10, and between vessel 10 and pump 5 when system 1 is operated in multi-pass mode. Some non-limiting examples of such heat transfer devices are shell, tube, plate, and coil heat exchangers, as are known in the art.

Pumps. Pump 5 is configured for either continuous or semi-continuous operation, and may be any suitable pumping device that is capable of providing greater than 203 kPa (2 atm) pressure, preferably greater than 304 kPa (3 atm) pressure, to allow controlled flow through HSD 40 and system 1. For example, a Roper Type 1 gear pump, Roper Pump Company (Commerce Ga.) Dayton Pressure Booster Pump Model 2P372E, Dayton Electric Co (Niles, Ill.) is one suitable pump. Preferably, all contact parts of the pump comprise stainless steel, or, when corrosive substances such as concentrated nitric and sulfuric acids will be pumped, the contact surfaces may be gold plated. In some embodiments of the system, pump 5 is capable of pressures greater than about 2027 kPa (20 atm). In addition to pump 5, one or more additional, high pressure pumps (not shown) may be included in the system illustrated in FIG. 1. For example, a booster pump, which may be similar to pump 5, may be included between HSD 40 and vessel 10 for boosting the pressure into vessel 10. As another example, a supplemental feed pump, which may be similar to pump 5, may be included in line 15 for introducing the concentrated acids, water, or additional reactants or a catalyst into vessel 10. An outlet line 24 may connect vessel 10 to line 21 for introducing acid catalyst into HSD 40 via pump 5 and line 13. As still another example, a compressor type pump may be positioned between line 17 and HSD 40 for recycling unreacted gases or vapors from vessel 10 to an inlet of the high shear device.

Process for Production of Nitrobenzene. In operation for the production of nitrobenzene by homogeneous liquid-liquid phase reaction of benzene with a mixture of concentrated nitric acid and concentrated sulfuric acid, the nitric acid and sulfuric acid are first combined in vessel 10. Vessel 10 may be operated in either continuous or semi-continuous flow mode, or it may be operated in batch mode. The contents of vessel 10 may be maintained at a specified bulk reaction temperature using suitable heating and/or cooling capabilities (e.g., cooling coils) and temperature measurement instrumentation. Pressure in the vessel may be monitored using suitable pressure measurement instrumentation, and the level of reactants in the vessel may be controlled using a level regulator (not shown), employing techniques that are known to those of skill in the art. The contents are stirred continuously or semi-continuously.

A stream of the concentrated acid mixture is withdrawn from vessel 10, and flows through line 24 into line 21, and is pumped through line 13 into HSD 40. In line 13, the acid mixture is combined with a liquid benzene stream. Alternatively, the benzene may be fed directly into HSD 40, instead of being combined with the acids in line 13. Pump 5 is operated to pump the acids through line 21, and to build pressure and feed HSD 40, providing a controlled flow throughout high shear mixer (HSD) 40 and system 1. In some embodiments, pump 5 increases the pressure of the benzene stream to greater than 203 kPa (2 atm), preferably greater than about 304 kPa (3 atm).

In some embodiments, the molar ratio of nitric to sulfuric is 1:2. In some embodiments, benzene is continuously fed into the nitric and sulfuric acid stream 13 to form the feed stream to HSD 40. In some cases, the molar ratio of benzene to acid mixture are one part benzene to one part nitric acid to two parts sulfuric acid in the feed stream, for example. Water may also be introduced with the acid, or it may be introduced independently. The actual ratio of raw materials depends on the desired selectivity and operating temperatures and pressures.

After pumping, the benzene and acid reactants are mixed within HSD 40, which serves to create a fine dispersion or emulsion of the benzene in the concentrated acid mixture. In HSD 40, the benzene and the concentrated acids are highly dispersed such that a nanoemulsion of the benzene is formed. As used herein, the term "dispersion" refers to a liquefied mixture that contains two distinguishable substances (or phases) that will not readily mix and dissolve together. A dispersion comprises a continuous phase (or matrix), which holds therein discontinuous droplets, bubbles, and/or particles of the other phase or substance. The term dispersion may thus refer to foams comprising gas bubbles suspended in a liquid continuous phase, emulsions in which droplets of a first liquid are dispersed throughout a continuous phase comprising a second liquid with which the first liquid is immiscible, and continuous liquid phases throughout which solid particles are distributed. The term "dispersion" encompasses continuous liquid phases throughout which gas bubbles are distributed, continuous liquid phases throughout which solid particles (e.g., solid catalyst) are distributed, continuous phases of a first liquid throughout which droplets of a second liquid that is substantially insoluble in the continuous phase are distributed, and liquid phases throughout which any one or a combination of solid particles, immiscible liquid droplets, and gas bubbles are distributed. Hence, a dispersion can exist as a homogeneous mixture in some cases (e.g., liquid/liquid phase), or as a heterogeneous mixture (e.g., gas/liquid, solid/liquid, or gas/solid/liquid), depending on the nature of the materials selected for combination.

An emulsion or nanoemulsion is sometimes also referred to herein as a "dispersion." For the purposes of this disclosure, a nanoemulsion is an emulsion of immiscible liquid phases in which the sizes of the particles in the dispersed phase are less than 1000 nanometers (i.e., <1 micron). For example, disperser IKA® model DR 2000/4, a high shear, three stage dispersing device configured with three rotors in combination with stators, aligned in series, is used to create the dispersion of benzene in the liquid medium comprising the concentrated nitric and sulfuric acids (i.e., "the reactants"). The rotor/stator sets may be configured as illustrated in FIG. 2, for example. For some applications, the direction of rotation of the generators may be opposite that shown by arrow 265 (e.g., clockwise or counterclockwise about axis of rotation 260). The combined reactants enter the high shear mixer via line 13 and enter a first stage rotor/stator combination having circumferentially spaced first stage shear openings. In some applications, the direction of flow of the reactant stream entering inlet 205 corresponds to the axis of rotation 260. The coarse dispersion exiting the first stage enters the second rotor/stator stage, having second stage shear openings. The reduced particle-size dispersion emerging from the second stage enters the third stage rotor/stator combination having third stage shear openings. The dispersion exits the high shear mixer via line 18. In some embodiments, the shear rate increases stepwise longitudinally along the direction of the flow. For example, in some embodiments, the shear rate in the first rotor/stator stage is greater than the shear rate in subsequent stage(s). In other embodiments, the shear rate is substantially constant along the direction of the flow, with the stage or stages being the same. If the high shear mixer includes a PTFE seal, for example, the seal may be cooled using any suitable technique that is known in the art. For example, the reactant stream flowing in line 13 may be used to cool the seal and in so doing be preheated as desired prior to entering the high shear mixer.

The rotor of HSD 40 is set to rotate at a speed commensurate with the diameter of the rotor and the desired tip speed. As described above, the high shear mixer (e.g., colloid mill) has either a fixed clearance between the stator and rotor or has adjustable clearance. HSD 40 serves to intimately mix the benzene and the concentrated acids. In some embodiments of the process, the transport resistance of the reactants is reduced by operation of the high shear mixer such that the velocity of the reaction is increased by greater than a factor of about 5. In some embodiments, the velocity of the reaction is increased by at least a factor of 10. In some embodiments, the velocity is increased by a factor in the range of about 10 to about 100 fold. In some embodiments, HSD 40 delivers at least 300 L/h with a power consumption of 1.5 kW at a nominal tip speed of at least 22.9 m/sec (4500 ft/min), and which may exceed 40 m/sec (7900 ft/min). In some embodiments, the mixture is subjected to a shear rate greater than 20,000 $s^{-1}$.

Although measurement of instantaneous temperature and pressure at the tip of a rotating shear unit or revolving element in HSD 40 is difficult, it is estimated that the localized temperature seen by the intimately mixed reactants is in excess of 500° C. and at pressures in excess of 500 kg/$cm^2$ under cavitation conditions. The high shear mixing results in formation of an emulsion or nanoemulsion in which the dispersed benzene-containing particles are micron or submicron-sized particles (i.e., mean diameter less than one micron). In some embodiments, the resultant dispersion has an average particle size less than about 1.5 μm. In some embodiments, the mean particle size is in the range of about 0.4 μm to about 1.5 μm. In some embodiments, the dispersion is a nanoemulsion in which the mean diameter of the particles is less than 1 micron in size. In some embodiments, the mean particle size is less than about 400 nm, in the range of about 200 nm to about 400 nm, or may be about 100 nm in some cases. Accordingly, the dispersion exiting HSD 40 via line 18 comprises micron and/or submicron-sized particles. In many embodiments, the emulsion is able to remain dispersed at atmospheric pressure for at least 15 minutes.

Once dispersed, the resulting emulsion exits HSD 40 via line 18 and feeds into vessel 10, as illustrated in FIG. 1. Conversion of benzene to nitrobenzene will occur whenever suitable time, temperature and pressure conditions exist. In this sense the reaction may occur at any point in the path between HSD 40, vessel 10 and pump 5, as shown in FIG. 1, if the temperature and pressure conditions are favorable. As a result of the intimate mixing of the reactants prior to entering vessel 10, a significant portion of the chemical reaction may take place in HSD 40. A discrete reactor is usually desirable, however, to allow for increased agitation and heating and/or cooling of the bulk reactants, and increased residence time, if applicable. Accordingly, in some embodiments, vessel 10 may be used primarily for initial mixing of the acids, and subsequently for heating and separation of volatile reaction gases (i.e., vent gas) from the nitrobenzene product. Alternatively, or additionally, vessel 10 may serve as a primary reaction vessel where most or some portion of the total nitrobenzene product is produced. In either case, the chemical reaction comprises a heterogeneous liquid-liquid reaction in which the reactants are in the form of a very fine emulsion. The initial reaction to form the nitronium ion is homogeneous, however, the reactants (i.e., benzene and acid) comprise a two phase emulsion, or nanoemulsion. The reaction products are also in the form of a two phase emulsion or nanoemulsion. Operation of the process to avoid formation of dinitro compounds is desirable is many cases. Lower temperatures and adjusting the ratio of reactants is used to provide more selectivity to mono-nitrobenzene formation.

Catalyst. If a catalyst is used to promote the partial oxidation reaction in some embodiments, it may be introduced into the vessel via line 15, as an aqueous or nonaqueous slurry or stream. Alternatively, or additionally, catalyst may be added elsewhere in the system 1. For example, catalyst slurry may be injected into line 21. In some embodiments, the catalyst is added continuously to vessel 10 via line 15. Without wishing to be limited by theory, it is believed that sub-micron particles or bubbles dispersed in a liquid undergo movement primarily through Brownian motion effects. The bubbles in the product dispersion created by HSD 40 may have greater mobility through boundary layers of any catalyst particles, thereby facilitating and accelerating the catalytic reaction through enhanced transport of reactants.

The bulk or global operating temperature of the reactants is desirably maintained below their flash points. In some embodiments, the operating conditions of system 1 comprise a temperature in the range of from about 20° C. to about 230° C. In some embodiments, the temperature is less than about 200° C. In some embodiments, the temperature is in the range of from about 160° C. to 180° C. In specific embodiments, the reaction temperature in vessel 10, in particular, is in the range of from about 155° C. to about 160° C. In some embodiments, the reaction pressure in vessel 10 is in the range of from about 203 kPa (2 atm) to about 5573 kPa-6080 kPa (55-60 atm). In some embodiments, reaction pressure is in the range of from about 811 kPa (8 atm) to about 1520 kPa (15 atm). In some embodiments, the reaction pressure is less than 600 kPa (6 atm).

The dispersion may be further processed prior to entering vessel 10, if desired. The contents of vessel 10 are stirred continuously or semi-continuously, the temperature of the reactants is controlled (e.g., using a heat exchanger), and the fluid level inside vessel 10 is regulated using standard techniques. Nitrobenzene may be produced either continuously, semi-continuously or batch wise, as desired. Any reaction gas that is produced exits reactor 10 via gas line 17. This gas stream may comprise unreacted benzene vapor, nitrobenzene, sulfuric acid and volatile side reaction products, for example. The reaction gas removed via line 17 may be further treated and vented, or the components may be recycled, as desired. For example, all or a portion of any unreacted benzene and acid vapors in line 17 may be transferred via line 19 using a compression type pump back into HSD 40 for further mixing and reaction.

The reaction product stream comprising non-converted liquid benzene, nitrobenzene, and any derivatives and byproducts (e.g., dinitrobenzene and nitrophenols) exits vessel 10 by way of line 16. In some embodiments, the reaction product stream may be directed into a settling tank 50 for separation and removal of a supernatant containing nitrobenzene 55 and unreacted benzene 60. The nitrobenzene product stream 55 may be recovered and further processed as known in the art. For example, the nitrobenzene product stream 55 may serve as a chemical feed stock to a system/process 80 for synthesizing aniline.

Multiple Pass Operation. Referring still to FIG. 1, the system is configured for single pass or multipass, wherein, after the initial mixing of the acids in vessel 10 and commencement of the process, the output from line 16 of vessel 10 goes directly to recovery of the nitrobenzene or to further processing. In some embodiments it may be desirable to pass the contents of vessel 10, or a liquid fraction containing unreacted benzene, through HSD 40 during a second pass. In this case, the dispersion and the nitrobenzene product may be returned via lines 24 and 21, pump 5, and line 13, to HSD 40, for further dispersion and reaction. Additional acid or water may be injected via line 22 into line 13, or it may be added directly into the high shear mixer (not shown), if needed.

In some embodiments, two or more high shear devices like HSD 40, or they may be configured differently, are aligned in series, and are used to further enhance the reaction. Their operation may be in either batch or continuous mode. In some instances in which a single pass or "once through" process is desired, the use of multiple high shear devices in series may also be advantageous. In some embodiments where multiple high shear devices are operated in series, vessel 10 may be omitted. When multiple high shear devices 40 are operated in series, additional reactant(s) may be injected into the inlet feed stream of each device. In some embodiments, multiple high shear devices 40 are operated in parallel, and the outlet dispersions therefrom are introduced into one or more vessel 10.

The application of enhanced mixing of the reactants by HSD 40 potentially causes greater conversion of benzene to nitrobenzene in some embodiments of the process. In some embodiments, the enhanced mixing potentiates an increase in throughput of the process stream. In some embodiments, the high shear mixing device is incorporated into an established process, thereby enabling an increase in production (i.e., greater throughput). In contrast to some existing methods that attempt to increase the degree of conversion of benzene by increasing reactor pressures, the superior dissolution and/or emulsification provided by external high shear mixing may allow in many cases a decrease in overall operating pressure while maintaining or even increasing reaction rate. Without wishing to be limited to a particular theory, it is believed that the level or degree of high shear mixing is sufficient to increase rates of mass transfer and may also produce localized non-ideal conditions that enable reactions to occur that might not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," *Current Science* 91 (No. 1): 35-46 (2006). The high shear mixing device of certain embodiments of the present system and methods is operated under what is believed to be cavitation conditions effective to dissociate the reactants into free radicals which then form into nitrobenzene product.

In some embodiments, the system and processes described herein enable design of a smaller and/or less capital intensive process than previously possible without the use of external high shear mixer 40. Potential advantages of certain embodiments of the disclosed processes are reduced operating costs and increased production from an existing process. Certain embodiments of the disclosed processes additionally offer the advantage of reduced capital costs for the design of new processes. Potential benefits of some embodiments of this system and methods for the production of nitrobenzene include, but are not limited to, faster cycle times, increased throughput, higher conversion, reduced operating costs and/or reduced capital expense due to the possibility of designing smaller reactors and/or operating the nitrobenzene production process at lower temperature and/or pressure.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of broader terms such as comprises, includes, having, etc. should be understood to provide support for narrower terms such as consisting of, consisting essentially of, comprised substantially of, and the like. Accordingly, the scope of protection is not limited by the description set out above but is only limited by the claims which follow, that scope including all equivalents of the subject matter of the claims. Each and every original claim is incorporated into the specification as an embodiment of the invention. Thus, the claims are a further description and are an addition to the preferred embodiments of the present invention. The disclosures of all patents, patent applications, and publications cited herein are hereby incorporated by reference, to the extent they provide exemplary, procedural or other details supplementary to those set forth herein.

What is claimed is:

1. A system for production of nitrobenzene, the system comprising:
   at least one high shear mixing device configured for producing a nanoemulsion comprising benzene-containing particles dispersed in a mixture of concentrated nitric acid and concentrated sulfuric acid, wherein said particles have a mean diameter of less than 1 micron;
   a pump configured for delivering a pressurized liquid stream comprising a mixture of concentrated nitric acid and concentrated sulfuric acid and benzene to said at least one high shear mixing device; and
   a vessel configured for receiving said nanoemulsion from said at least one high shear mixing device, wherein the vessel comprises an inlet for the nano emulsion, a gas outlet configured for removal of gas from the vessel, an outlet for a reaction product comprising nitrobenzene and an outlet line fluidly connecting the vessel with the at least one high shear mixing device whereby material may be transferred from the vessel to the at least one high shear mixing device.

2. The system of claim 1 wherein said at least one high shear mixing device is configured to produce said nanoemulsion comprising benzene-containing particles dispersed in a mixture of concentrated nitric acid and concentrated sulfuric acid, wherein said particles have a mean diameter less than about 400 nm, and wherein the nanoemulsion further comprises greater than 3.0 wt % nitric acid.

3. The system of claim 1 wherein said at least one high shear mixing device is configured to produce a nanoemulsion comprising nitrobenzene particles having a mean diameter in the range of from about 200 nm to about 400 nm.

4. The system of claim 1 wherein said at least one high shear mixing device is configured to produce a nanoemulsion comprising nitrobenzene particles having a mean diameter of no more than 100 nm.

5. The system of claim 1 wherein said at least one high shear mixing device comprises at least one rotor and at least one complementarily-shaped stator and wherein said device is configured for operating at a tip speed of at least 22.9 m/sec, wherein the tip speed is defined as $\pi Dn$, where D is the diameter of the at least one rotor and n is the frequency of revolution.

6. The system of claim 5 wherein said at least one high shear mixing device is configured for operating at a flow rate of at least 300 L/h.

7. The system of claim 5 wherein said at least one high shear mixing device is operable to produce a local pressure of at least about 1034 MPa at said rotor tip.

8. The system of claim 1 wherein said at least one high shear mixing device comprises a rotor tip and said device is configured for operating at a tip speed of at least 40 m/sec, wherein the tip speed is defined as $\pi Dn$, where D is the diameter of the at least one rotor and n is the frequency of revolution.

9. The system of claim 1 wherein said at least one high shear mixing device is configured to provide an energy expenditure of greater than 1000 W/m$^3$.

10. The system of claim 1 wherein said at least one high shear mixing device is configured to subject said benzene, nitric acid and sulfuric acid to a shear rate of at least 20,000 s$^{-1}$, wherein the shear rate is defined as the tip speed divided by the shear gap, and wherein the tip speed is defined as $\pi Dn$, where D is the diameter of the at least one rotor and n is the frequency of revolution.

11. The system of claim 1 wherein said vessel is operable to subject said nanoemulsion to reaction conditions comprising a pressure in the range of 203 kPa to 6080 kPa and a temperature in the range of about 20° C. to about 230° C., whereby at least a portion of said benzene is nitrated to form nitrobenzene.

12. The system of claim 1 wherein said gas outlet is configured for removal of a gas consisting of components selected form the group consisting of unreacted benzene vapor, nitrobenzene, sulfuric acid, volatile side reaction products, and combinations thereof from said vessel.

13. The system of claim 1 wherein the outlet line fluidly connecting the vessel with the at least one high shear mixing device is connected with a recycle line connecting said vessel with said pump, whereby unspent nitric acid, sulfuric acid, or both may be recycled to said at least one high shear mixing device.

14. The system of claim 1 wherein said vessel further comprises an inlet configured for introduction of at least one component selected from the group consisting of water, catalyst, concentrated sulfuric acid, and concentrated nitric acid to said vessel during startup, continuously, or both.

15. The system of claim 1 wherein said pump is configured for delivering a pressurized liquid stream comprising a mixture of concentrated nitric acid and concentrated sulfuric acid to said at least one high shear mixing device at a molar ratio of 1:2.

16. The system of claim 15 wherein said nanoemulsion comprises a molar ratio of benzene to nitric acid of 1:1.

17. A system for production of nitrobenzene, the system comprising:

at least one high shear mixing device configured for producing a nanoemulsion comprising benzene-containing particles dispersed in a mixture of concentrated nitric acid and concentrated sulfuric acid, wherein presence of nitric acid within the nanoemulsion is greater than 3.0 wt %;

a pump configured for delivering a pressurized liquid stream comprising a mixture of concentrated nitric acid and concentrated sulfuric acid and benzene to said at least one high shear mixing device;

a vessel configured for receiving said nano emulsion from said at least one high shear mixing device, wherein the vessel comprises an inlet for the nano emulsion, a gas outlet configured for removal of gas from the vessel, an outlet for a reaction product comprising nitrobenzene, and an outlet line fluidly connecting the vessel with the at least one high shear mixing device, whereby material may be transferred from the vessel to the at least one high shear mixing device; and a separator tank downstream said vessel and fluidly connected to the vessel outlet for reaction product comprising nitrobenzene, said separator tank configured to separate a supernatant comprising nitrobenzene from unreacted benzene in the liquid reaction product.

18. The system of claim 17 further comprising a recycle line fluidly connecting said separator tank with said at least one high shear mixing device for recycle of the separated unreacted benzene to said at least one high shear mixing device.

19. The system of claim 17 further comprising aniline production apparatus downstream of said separator tank and fluidly connected therewith, said aniline production apparatus operable to produce aniline from said supernatant comprising nitrobenzene.

20. A system for production of nitrobenzene, the system comprising:

at least one high shear mixing device configured for producing a nanoemulsion comprising benzene-containing particles dispersed in a mixture of concentrated nitric acid and concentrated sulfuric acid;

a pump configured for delivering a pressurized liquid stream comprising a mixture of concentrated nitric acid and concentrated sulfuric acid and benzene to said high shear mixing device;

a vessel operated under a pressure of greater than 304 kPa and less than 6080 kPa, the vessel configured for receiving said nanoemulsion from said high shear mixing device, wherein the vessel comprises an inlet for the nanoemulsion, a gas outlet configured for removal of gas from the vessel, an outlet for a reaction product comprising nitrobenzene, an outlet line fluidly connecting the vessel with the at least one high shear mixing device, whereby material may be transferred from the vessel to the at least one high shear mixing device, and a recycle line fluidly connecting said gas outlet and said at least one high shear mixing device.

* * * * *